United States Patent [19]
Balzar et al.

[11] Patent Number: 6,036,679
[45] Date of Patent: Mar. 14, 2000

[54] INDIVIDUALLY WRAPPED ABSORBENT ARTICLE

[75] Inventors: Tammy Jo Balzar, Menasha; Janet Jessie Larsen, Neenah; James Dell Milner, Appleton; Valerie Victoria Finch, Neenah; Pamela Jean DeShaney, Readfield, all of Wis.

[73] Assignee: Kimberly-Clark Worldwide, Inc., Neenah, Wis.

[21] Appl. No.: 09/057,875

[22] Filed: Apr. 9, 1998

[51] Int. Cl.[7] .............................. A61F 13/15; A61M 5/24
[52] U.S. Cl. ...................... 604/387; 604/358; 604/385.1; 206/438; 206/440
[58] Field of Search ..................................... 604/393, 387, 604/385.1, 358; 206/440, 438, 824; 229/87.05

[56] References Cited

U.S. PATENT DOCUMENTS

| | | | |
|---|---|---|---|
| H1363 | 10/1994 | Leeker | 206/440 |
| H1454 | 6/1995 | Cucuzza et al. | |
| 3,561,593 | 2/1971 | Ruda | 206/57 |
| 3,698,549 | 10/1972 | Glassman | 206/63.2 R |
| 3,973,567 | 8/1976 | Srinivasan et al. | 128/290 R |
| 4,170,305 | 10/1979 | Hull, Jr. et al. | 206/606 |
| 4,556,146 | 12/1985 | Swanson et al. | 206/440 |
| 5,181,610 | 1/1993 | Quick et al. | 206/447 |
| 5,445,454 | 8/1995 | Barkhorn | 383/207 |

FOREIGN PATENT DOCUMENTS

| | | | |
|---|---|---|---|
| 0 750 896 A3 | 1/1997 | European Pat. Off. | A61F 13/15 |
| 0 798 229 A1 | 1/1997 | European Pat. Off. | |
| 4127411 C1 | 1/1992 | Germany | |
| 2273279 | 6/1994 | United Kingdom | B65D 85/16 |
| 2273279 | 9/1994 | United Kingdom | |
| 2300402 | 6/1996 | United Kingdom | |
| WO 94/14396 A1 | 6/1994 | WIPO | |
| WO 97/12572 A1 | 4/1997 | WIPO | A61F 13/15 |

OTHER PUBLICATIONS

Patent Cooperation Treaty Search Report from the International Search Authority, Interntional Application No. PCT/US 99/07684 dated Jul. 16, 1999.

*Primary Examiner*—John G. Weiss
*Assistant Examiner*—Miley Craig Peppers, III
*Attorney, Agent, or Firm*—Thomas M. Parker

[57] ABSTRACT

This invention relates to an individually wrapped absorbent article. The absorbent article has first and second ends, first and second sides, and first and second major surfaces. The second major surface of the absorbent article has a garment attachment adhesive secured thereto. A release strip is removably secured to the garment attachment adhesive to prevent premature contamination of the garment attachment adhesive before the absorbent article is secured to an undergarment. The absorbent article is wrapped in a wrapper having first and second ends, first and second sides, and first and second major surfaces. A first major surface of the wrapper is positioned adjacent to the release strip with the first and second ends of the wrapper extending beyond the first and second ends, respectively, of the absorbent article. In addition, the first and second sides of the wrapper extend beyond the first and second sides, respectively, of the absorbent article. An attachment device is secured to the second major surface of the wrapper approximate the first ends thereof. The wrapper and absorbent article are then folded together about two fold axes such that the first major surface of the wrapper contacts the attachment device and is releasably secured thereto to form a package. The package has first and second side edges aligned approximately parallel to the first and second sides of the absorbent article. The first and second side edges of the package are bonded together by first and second seals, respectively, and at least one line of perforations is formed in the wrapper which provides an easy open feature for the package. Alternatively, the package can contain two lines of perforations which are aligned adjacent to the first and second seals which allow the wrapper to be torn open into three separate and distinct sections.

5 Claims, 7 Drawing Sheets

INDIVIDUALLY WRAPPED ABSORBENT ARTICLE

FIELD OF THE INVENTION

This invention relates to an individually wrapped absorbent article such as a catamenial pad. More specifically, this invention relates to an individually wrapped absorbent article having one or more lines of perforations which allow the wrapper to be easily opened so that the absorbent article can be easily and quietly removed.

BACKGROUND OF THE INVENTION

Absorbent articles such as sanitary napkins, panty liners, and other types of catamenial devices are used to absorb menses and other body fluids. Such absorbent articles are primarily disposable and are used during a women's menstrual cycle. In addition, disposable absorbent articles are used between menstrual periods for light incontinence purposes. Since many of these absorbent articles are carried in a woman's purse or pocket prior to use, it is advantageous to individually wrap each article so as to keep it clean. By individually packaging each absorbent article, the manufacturer can be assured that the article will not become contaminated by makeup, perfume, dirt, etc. Because of this, many absorbent articles commercially sold today are individually packaged.

Generally, the wrapper consists of a thin sheet of thermoplastic material, such as polyethylene, which is folded around the absorbent article and is then sealed by the use of heat and/or pressure, by ultrasonics or an adhesive, to form a package. The package is designed to be opened by breaking or tearing the material at or adjacent the seal so as to remove the absorbent article. Normally, the thermoplastic material is designed to tear adjacent to the seal. However, when this occurs, the thermoplastic material acquires a ragged appearance and the tearing operation can be noisy. Most woman desire a package which can be quietly opened to avoid any embarrassing moments. In addition, it has been found that some seals are of a frangible nature such that they will come apart prior to use and therefore allow contamination to enter and contact the absorbent article. This is a detriment in that the consumer expects the absorbent article to be clean in appearance when she opens the package.

Another use of the wrapper is to enclose a soiled sanitary napkin after it has been used by the consumer so that it can be discretely disposed. For this reason, it is advantageous to design a package which can be opened such that a single piece of wrapper material remains which can be used to wrap up a soiled sanitary napkin prior to its disposal.

In view of the above, it has been recognized that there is a need for an individually wrapped absorbent article which has an easy open feature and which can be quietly and discreetly opened. It is also advantageous to offer an individually wrapped absorbent article having one or more lines of perforations which enable the wrapper to be cleanly torn apart so that no ragged edges are present.

SUMMARY OF THE INVENTION

Briefly, this invention relates to an individually wrapped absorbent article such as a catamenial pad. The absorbent article has first and second ends, first and second longitudinal sides, and first and second major surfaces. The second major surface of the absorbent article has a garment attachment adhesive secured thereto. A release strip is removably secured to the garment attachment adhesive to prevent premature contamination of the garment adhesive before the absorbent article is secured to the crotch portion of an undergarment. A wrapper having first and second ends, first and second longitudinal sides, and first and second major surfaces is positioned with its first major surface contacting the release strip.

An attachment device is secured to the second major surface of the wrapper approximate the first end thereof. The wrapper and the absorbent article are then folded together about two fold axes such that the first major surface of the wrapper contacts the attachment device and is releasably secured thereto to form a package. The package has first and second side edges aligned approximately parallel to the first and second longitudinal sides of the absorbent article, respectively. The individually wrapped absorbent article also contains a first seal and a second seal which secure the first and second side edges of the package together. The package further contains at least one line of perforations formed in the wrapper which provide an easy open feature for the package.

The general object of this invention is to provide an individually wrapped absorbent article, such as a sanitary napkin. A more specific object of this invention is to provide an individually wrapped absorbent article having at least one line of perforations which permit easy opening of the wrapper once the consumer is ready to use the absorbent article.

Another object of this invention is to provide an individually wrapped absorbent article which contains first and second lines of perforations formed adjacent to the first and second seals so as to provide an easy open feature for the package.

A further object of this invention is to provide a quick and quiet means of opening individually wrapped absorbent article.

Still another object of this invention is to provide an individually wrapped absorbent article which can be manufactured very reasonably and economically.

Still further, an object of this invention is to provide an individually wrapped absorbent article, such as a sanitary napkin, wherein the opened wrapper can be used to dispose of a soiled sanitary napkin.

Other objects and advantages of the present invention will become more apparent to those skilled in the art in view of the following description and the accompanying drawings.

DETAILED DESCRIPTION OF THE PREFERRED EMBODIMENTS

Figure 1:
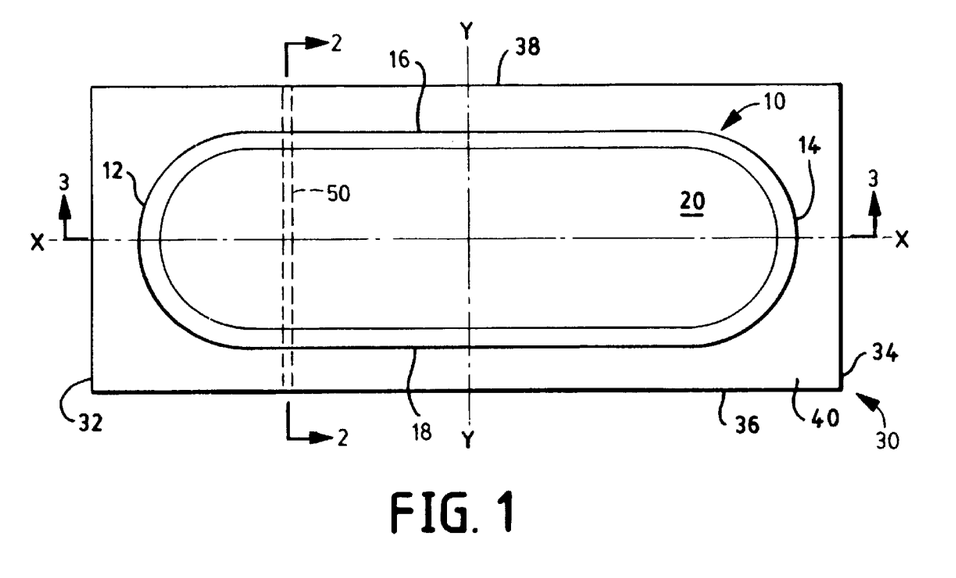
FIG. 1 is a top view of an absorbent article positioned on an elongated wrapper such that the ends and sides of the absorbent article are located inward of the perimeter of the wrapper.
Figure 2:
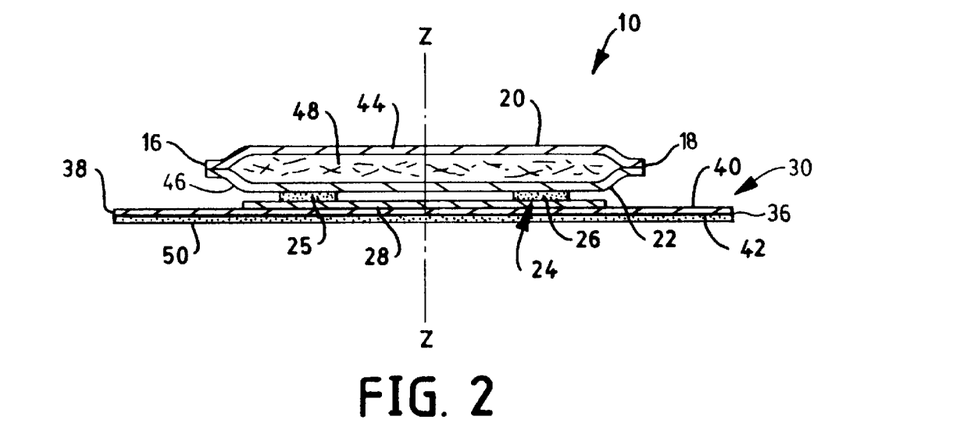
FIG. 2 is a cross-sectional view of the absorbent article and wrapper shown in FIG. 1 taken along line 2—2 and which reveal the construction of the absorbent article and the presence of two strips of garment attachment adhesive covered by a releasable peel strip.

Referring to FIGS. 1 and 2, an absorbent article 10 is shown. The absorbent article 10 can be a sanitary napkin, a panty liner, an incontinence device, or any other type of catamenial device. The absorbent article 10 has a first end 12 and a second end 14. The absorbent article 10 also has a first side 16 and a second side 18. The first and second sides, 16 and 18 respectively, are the longitudinal sides of the elongated absorbent article and they can be equally spaced apart from a longitudinal center axis x—x. The absorbent article 10 also has a transverse central axis y—y and a vertical central axis z—z. It should be noted that the absorbent article 10 can have a wrapped configuration or have an outer peripheral seal as is depicted in FIGS. 1 and 2.

The absorbent article 10 further has a first major surface 20 and a second major surface 22. Secured to at least a portion of the second major surface 22 is a garment attachment adhesive 24. The garment attachment adhesive 24 can be a single band of adhesive or it can be two spaced apart strips 25 and 26, as are shown in FIG. 2. Alternatively, the garment attachment adhesive 24 can be three separate strips or consist of a swirl pattern of adhesive which encompasses a major portion of the second major surface 22 of the absorbent article 10.

A release strip 28, also known as a releasable peel strip, is removably secured to the garment attachment adhesive 24 and serves to prevent premature contamination of the adhesive 24 before the absorbent article 10 is secured to the crotch portion of an undergarment. The release strip 28 can also be attached to a wrapper 30. When this is done, the release strip 28 will separate from the absorbent article 10 when the wrapper 30 is removed. Normally, when the absorbent article 10 is a sanitary napkin, the garment attachment adhesive 24 is designed to be secured to the inner crotch portion of an undergarment so as to keep the sanitary napkin in register with the body.

The absorbent article 10, with its attached release strip 28, is positioned on a wrapper 30. The wrapper 30 can be formed from a thermoplastic film or a silicone coated paper. Two preferred films for the wrapper 30 are polyethylene and polypropylene. The wrapper 30 can also be formed as a laminate from two or more layers of a film or nonwoven material. For example, the wrapper 30 can be formed as a two layer laminate consisting of a layer of polyethylene film and a layer of nonwoven materials, such as spunbond. "Spunbond" is a material available from Kimberly-Clark Corporation having an office at 401 N. Lake Street Neenah, Wis. 54956. The wrapper should have a thickness of less than about 5 millimeters (mm), and preferably, less than about 2 mm.

The wrapper 30 has a first end 32 and a second end 34, a first side 36 and a second side 38, and a first major surface 40 and a second major surface 42. The first major surface 40 of the wrapper 30 is positioned adjacent to and in contact with the release strip 28. When the wrapper 30 is attached to the absorbent article 10, the first and second ends, 34 and 36 respectively, of the wrapper 30 will extend outward beyond the first and second ends, 12 and 14 respectively, of the absorbent article 10. In addition, the first and second sides, 36 and 38 respectively, of the wrapper 30 will extend beyond the first and second sides, 16 and 18 respectively, of the absorbent article 10. In this position, as shown in FIG. 1, the entire outer periphery of the absorbent article 10 will be located within the periphery of the wrapper 30.

It should be mentioned that the absorbent article 10 can include a cover 44, a baffle 46 and an absorbent 48. The cover 44 should be liquid permeable and can be formed from a nonwoven material such as spunbond or a perforated thermoplastic film. The baffle 46 should be liquid-impermeable and can be formed out of a thin layer of thermoplastic film, such as polyethylene. The liquid permeable cover 44 and the liquid-impermeable baffle 46 can be peripherally sealed together to enclose the absorbent 48 to form the absorbent article 10. Alternatively, the cover 44 can be wrapped around both the absorbent 48 and the baffle 46 to form a wrapped pad.

The absorbent 48 is designed to absorb body exudates, including menstrual fluid, blood, urine, and other body fluids. The absorbent 48 can consist of one or more layers of absorbent material. The layers can consist of similar materials or different materials. Suitable materials for the absorbent 48 include cellulose, wood pulp fluff, rayon, cotton, and meltblown polymers such as polyester, polypropylene or coform. Coform is a meltblown air-formed combination of meltblown polymers, such as polypropylene, and absorbent staple fibers, such as cellulose. A preferred material is wood pulp fluff, for it is low in cost, relatively easy to form, and has great absorbency.

The absorbent 48 can also be formed from a composite comprised of a hydrophilic material that can be formed from various natural or synthetic fibers, wood pulp fibers, regenerated cellulose or cotton fibers, or a blend of pulp and other fibers. A preferred material is an airlaid tissue.

It is also possible and sometimes advantageous to insert a superabsorbent material into the absorbent 48 so as to increase its ability to absorb a large amount of fluid in relation to its own weight. Typical superabsorbents used in absorbent articles such as sanitary napkins, can absorb anywhere from 5 to 60 times their weight in body fluid. The superabsorbent materials can be inserted as particles or in sheet form. Hydroxyfunctional polymers have been found to be good superabsorbents for sanitary napkins. Such superabsorbents are commercially available from Dow Chemical, Hoechst-Celanese, and Stockhausen, Incorporated, among others, and are a partially neutralized salt of cross-linked copolymer of polyacrylic acid and polyvinyl alcohol having an absorbency under load value above 25. Other types of superabsorbent materials known to those skilled in the art can also be used.

Figure 3:
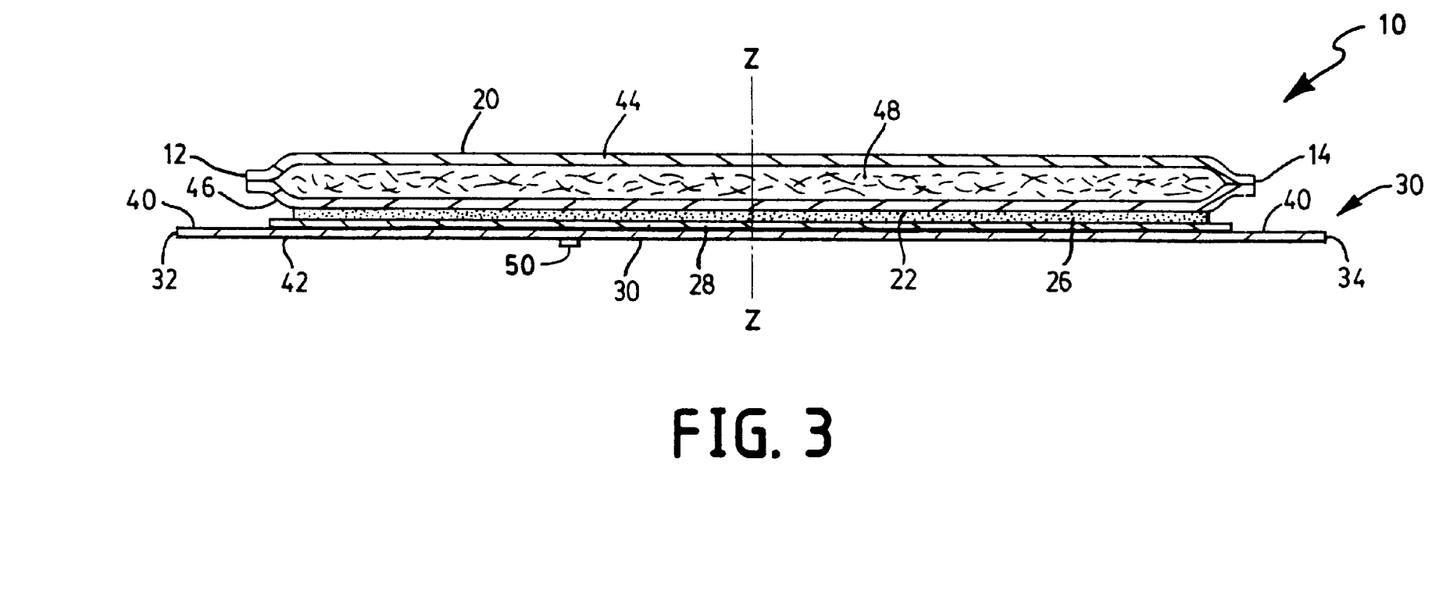
FIG. 3 is a cross-sectional view of the absorbent article and wrapper shown in FIG. 1 taken along line 3—3
Figure 4:
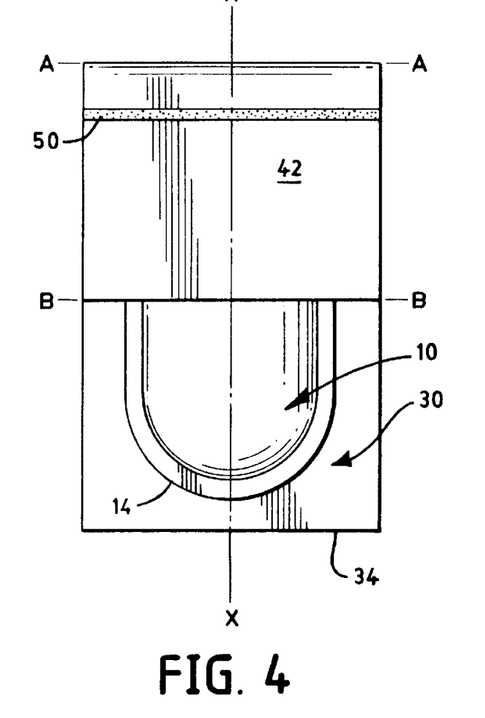
FIG. 4 is a top view of the absorbent article and wrapper being folded along a fold line A—A and revealing the location of the attachment device on the second major surface of the wrapper.

Referring to FIGS. 2–4, the wrapper 30 contains an attachment device 50 secured to the second major surface 42. The attachment device 50 can be a spot, line or strip of adhesive which has releasable properties such that a material attached to it can be separated without a great deal of force. The attachment device 50 is located near the first end 32 of the wrapper 30. By "near" it is meant that it may be within about 3 inches (about 76 mm) of the end 32, preferably, it is within about 2 inches (about 50 mm) of the end 32, and most preferably, it is within about 1.5 inches (about 38 mm) of the end 32. The wrapper 30 and the absorbent article 10 are designed to be folded together as a unit about two fold axes, such as depicted in FIG. 4. The two fold axes are designated as A—A and B—B. The two fold axes, A—A and B—B respectively, are located approximately one third of the distance from each of the first and second ends, 32 and 34 respectively, of the wrapper 30. However, the two fold axes, A—A and B—B do not have to be an equal distance from the first and second ends, 32 and 34 respectively. When the absorbent article 10 and the wrapper 30 are folded along the first fold axis A—A, the attachment device 50 will be exposed and is available for securement to the first major surface 40 upon folding both the wrapper 30 and absorbent article 10 along the second fold axes B—B.

Figure 5:
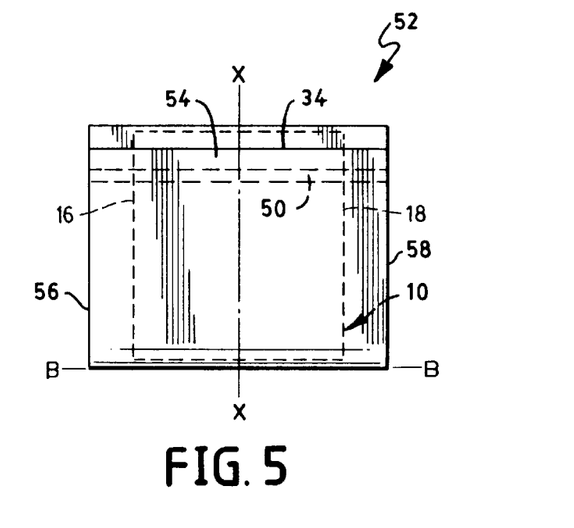
FIG. 5 is a top view of the absorbent article and wrapper after being folded along a second fold line B—B showing the first major surface of the wrapper contacting the attachment device to form a package.

Referring to FIG. 5, the folded wrapper 30 and absorbent article 10 are depicted such that the attachment device 50 will secure the first major surface 40 to the second major surface 42 of the wrapper 30 so as to form a package 52. When the package 52 is formed, the second end 34 of the wrapper 30 will extend beyond the attachment device 50 and form a flap 54. The flap 54 is important because it provides a means for the user to grasp the wrapper 30 between her thumb and fingers so as to release the first major surface 40 from the second major surface 42.

Still referring to FIG. 5, the package 52 has a first side edge 56 and a second side edge 58. The two side edges, 56 and 58 respectively, are spaced apart from one another and each is aligned adjacent to, and preferably, approximately parallel to the first and second sides 16 and 18, respectively, of the absorbent article 10. Another way of stating this is say that the longitudinal side edges 16 and 18 of the absorbent article 10 are aligned adjacent to the first and second side edges, 56 and 58 respectively, of the package 52.

Figure 6:
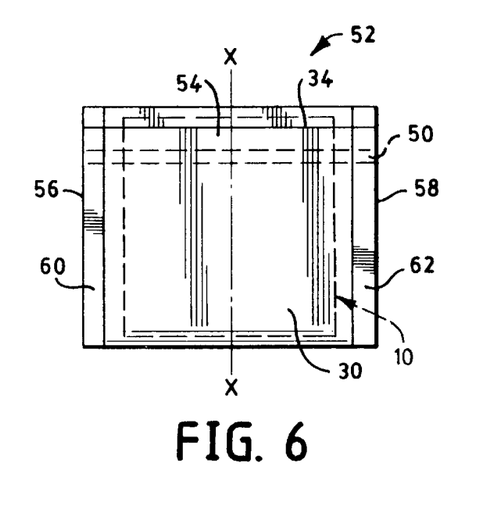
FIG. 6 is a top view of the package shown in FIG. 5 with the addition of first and second seals formed along the side edges of the package.

Referring to FIG. 6, the package 52 also contains a first seal 60 and a second seal 62 which secure the first and second side edges, 56 and 58 respectively, of the package 52 together. Preferably, the first and second seals, 60 and 62 respectively, can be formed by heat, heat and pressure, pressure, or by adhesive, or by the use of ultrasonic bonding or by other types of bonding methods known to those skilled in the art. Each of the first and second seals, 60 and 62 respectively, can be made to be a permanent seal. By a "permanent seal" it is meant that the material adjacent to the seal will tear, fracture or break before the seal separates. Alternatively, each of the first and second seals, 60 and 62 respectively, can be made to be a frangible seal. By "frangible" it is meant that the seal itself can break apart as one opens the package 52. For this invention, it is preferable that the first and second seals, 60 and 62 respectively, be of the permanent design such that the seals 60 and 62 will not break or tear, but the package 52 will be opened by tearing or opening at another location.

Figure 7:
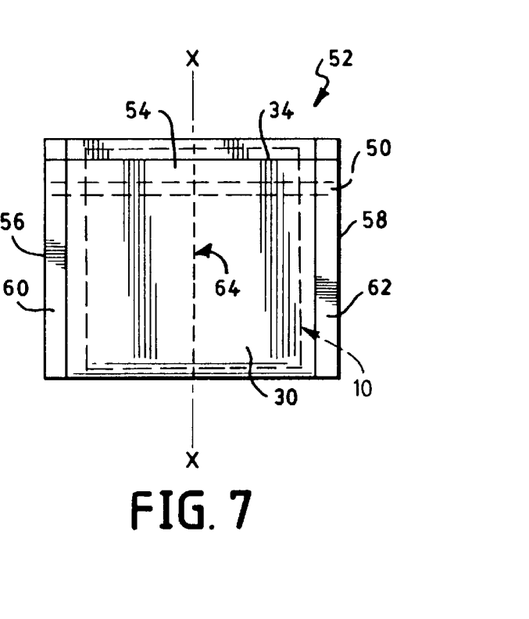
FIG. 7 is a top view of the sealed package shown in FIG. 6 with the addition of a line of perforations formed adjacent to the longitudinal centerline X—X.

Referring to FIG. 7, the package 52 further contains a line of perforations 64 which is formed in the wrapper 30 and provides an easy open feature to the package 52. In FIG. 7, the line of perforations 64 is coaxially aligned with the longitudinal central axis x—x and the line of perforations 64 extends from the first end 32 of the wrapper to the second end 34 of the wrapper 30. The line of perforations 64 is preferably linear but can be of a non-linear design if desired. For example, the line of perforations 64 can be arcuate or curved, for example, having a convex or concave shape. The line of perforations 64 can also be arranged at an angular disposition along its length, for example, it can have a stair-step or a saw-tooth configuration. Other unique configurations for the line of perforations 64 can also be utilized if desired.

The line of perforations 64 is comprised of a series of slits, each having a length of less than about 0.01 inches (about 0.2 mm) and preferably, less than about 0.001 inch (about 0.02 mm) and a width which is less than half of its length. The slits can be arranged along the line of perforations 64 such that they are equally spaced from one another or they can be arranged such that the spacing varies between slits along the length of the line of perforations 64. It should also be noted that the slits are preferably of the same length and width but they can be made to vary in length and/or width if desired. By varying the length and width of the individual slits, it may be possible to reduce or increase the amount of force necessary to tear the materials along the line of perforations 64. For example, it may be advantageous to configure the slits in the line of perforations 64 such that at an end, the slits will rapidly and quickly break apart while in the center portion of the line of perforations 64, a greater amount of force is required to separate the material.

In FIG. 7, the line of perforations 64 is located along the longitudinal central axis x—x. The package 52 can be opened by grasping opposite corners of the package 52 and pulling the wrapper 30 apart such that the material will tear along the line of perforations 64. Another way of opening the package 52 is to place either one or more fingers into the flap 54 so as to break the releasable attachment device 50. One method of inserting the fingers is to insert both the index finger and the middle finger into the flap 54. The thumb can then be positioned on the outside of the flap 54 such that the flap 54 is grasped between the finger and the thumb. The user's other hand would hold the package 52 at one corner such that as the fingers are inserted beyond the attachment device 50 and the material is pulled outward away from the package 52, the line of perforations will tear. Doing this, the wrapper 30 will tear completely along the line of perforations 64, thereby exposing the absorbent article 10.

Figure 8:
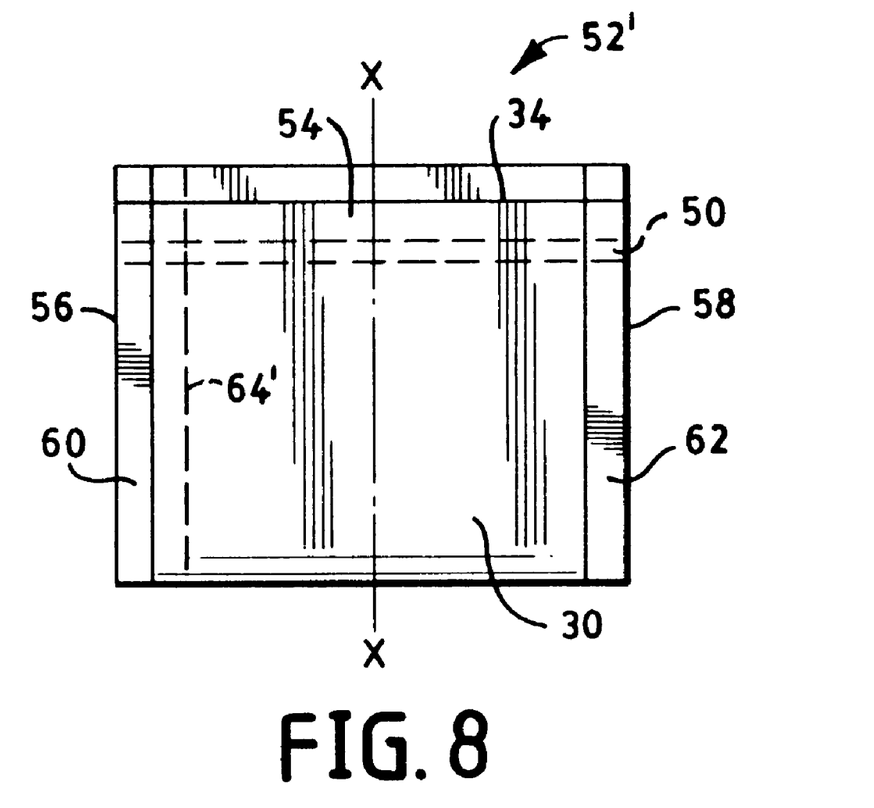
FIG. 8 is a top view of the sealed package shown in FIG. 6 with the addition of a line of perforations formed away from the longitudinal centerline X—X.

Referring to FIG. 8, an alternative embodiment of a package 52' is shown which as many of the same features as exhibited by the package 52. For purpose of discussion, similar elements are shown with identical numerals. For example, the package 52' has a first side edge 56, a second side edge 58, a first seal 60 and a second seal 62. The package 52' also has a second end 34 and a flap 54 which is located outbound of the attachment device 50. The difference between the packages 52 and 52' is that package 52' has a first line of perforations 64' which is offset from the longitudinal centerline x—x. In fact, the line of perforations 64' is located closer to the first seal 60 than to the second seal 62. By forming the line of perforations 64' adjacent to one of the seals 60 or 62, one can form a package 52' which can be opened by tearing or breaking the line of perforation 64' such that a pouch is available after the absorbent article 10 is removed. This pouch can then be used to discreetly dispose of a soiled absorbent article which the consumer may have been wearing. The consumer would fold the soil absorbent article and insert it into the pouch and then place the pouch in a trash container.

Figure 9:
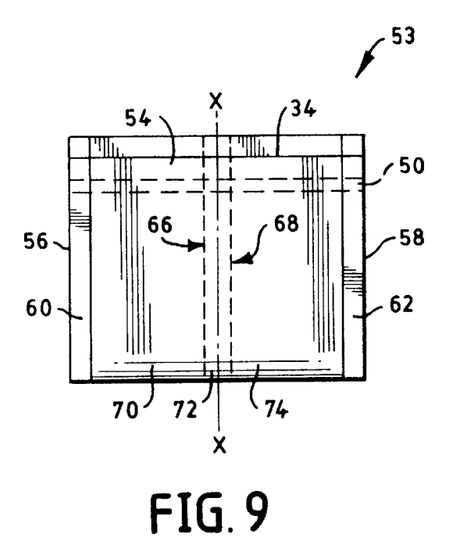
FIG. 9 is an alternative embodiment of the package shown in FIG. 6 depicting first and second spaced apart lines of perforations aligned adjacent to the longitudinal center axis X—X.

Referring to FIG. 9, another embodiment of a package 53 is shown which has many of the same features as exhibited by the package 52. For purpose of discussion, similar elements are shown with identical numerals. For example, the package 53 has a first side edge 56, a second side edge 58, a first seal 60 and a second seal 62. The package 53 also has a second end 34 and a flap 54 which is located outbound of the attachment device 50. The difference between the packages 52 and 53 is that package 53 has a first line of perforations 66 and a second line of perforations 68. The first and second lines of perforations, 66 and 68 respectively, are aligned adjacent to and, preferably, parallel to one another as well as being aligned approximately parallel to the longitudinal central axis x—x of the package 53. The first and second lines of perforations, 66 and 68 respectively, are located relatively close together. For example, the first and second lines of perforations, 66 and 68 respectively, can be within about 0.5 inches (about 13 mm) from one another, preferably they are located within about 0.25 inches (about 6.4 mm) of one another, and most preferably, they are located within about 0.1 inches (about 2.5 mm) of one another. The package 53 can be opened in a similar fashion as package 52 whereby only one of the lines of perforations 66 or 68 is broken. In this case, the wrapper 30 will be broken into two separate pieces. If the forces are such that both the first and second lines of perforations, 66 and 68 respectively, are broken simultaneously or sequentially, then the consumer will end up with three separate pieces of material designated 70, 72, and 74.

It should be noted that first and second lines of perforations, 66 and 68 respectively, can be constructed such that the slits forming the lines of perforations 66 and 68 can be identical in appearance along each of the lines of perforations. Alternatively, the slits can be varied such that the slits forming the first line of perforations 66 are different in size and/or configuration and/or spacing from those of the second line of perforations 68. One advantage of forming the first and second lines of perforations, 66 and 68 respectively, with different configurations of slits and spacing is to enable one to arrive at an arrangement where the package 53 can be easily opened while still ending up with only two pieces of wrapper, 70 and 74 respectively. This will eliminate the need for the end user to dispose of three separate pieces of material 70, 72 and 74.

Figure 10:
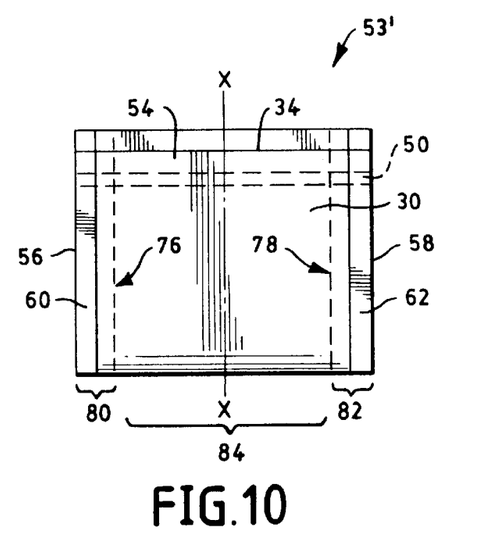
FIG. 10 is another alternative embodiment of the wrapper shown in FIG. 6 wherein the first and second lines of perforations are positioned adjacent to the first and second seals.

Referring to FIG. 10, still another embodiment of a package 53' is depicted which is similar to the package 53, except that it contains a first line of perforations 76 and a second line of perforations 78 which are spaced away from the longitudinal centerline x—x. The amount of spacing between the first and second lines of perforations, 76 and 78 respectively, is much greater than that shown in FIG. 9. In fact, the first line of perforations 76 is aligned adjacent to the first seal 60 and the second line of perforations 78 is aligned adjacent to the second seal 62. It should be noted that the first and second lines of perforations, 76 and 78 respectively, should be located relatively close to the respective first and second seals, 60 and 62 respectively. The distance between each of the lines of perforations, 76 and 78 respectively, and each of the respective first and second seals, 60 and 62 respectively, is less than about 0.5 inches (about 13 mm), preferably, less than about 0.25 inches (about 6.4 mm), and more preferably, less than about 0.1 inch (about 2.5 mm).

As stated above, when referring to the package 53 shown in FIG. 9, the first and second lines of perforations, 76 and 78 respectively, can be linear or non-linear. Preferably, the first and second lines of perforations, 76 and 78 respectively, are linear and are arranged approximately parallel to one another. In addition, the first and second lines of perforations, 76 and 78 respectively, can be arranged parallel to the first and second seals, 60 and 62 respectively. By forming the first and second lines of perforations, 76 and 78 respectively, as linear lines which are arranged approximately parallel to the first and second seals, 60 and 62 respectively, one can open the absorbent article 10 by tearing off the portions of the wrapper 80 and 82 which are located outboard of the first and second lines of perforations, 76 and 78 respectively. To do this, the consumer would grasp an end of the strip 80 between her index finger and her thumb and pull down and away such that the strip 80 is separated from the remainder of the wrapper 30. A similar motion can be used for the strip 82. This will leave a large portion of the wrapper 30, designated 84, which can then be opened by releasing the attachment device 50. The package 53' also has the added benefit in that it provides a large wrapper strip 84 which can be used to wrap a soiled sanitary napkin which the user may need to dispose of.

It should be mentioned that the first and second seals, 60 and 62 respectively, can be permanent seals such as is formed by the application of heat, heat and pressure, pressure or by using ultrasonics, adhesives, etc. By a "permanent seal" it is meant that the material adjacent to the bond is more likely to break before the seal 60 or 62 actually breaks. The first and second seals, 60 and 62 respectively, can also be made to be a frangible seal which is not as strong in peel strength as is a permanent seal. By "frangible seal" it is meant that the peel strength of the bond itself is less than that required to break or tear the adjacent wrapper material 30 and less than or equal to the force required to break the first and second lines of perforations, 76 and 78 respectively. When such a package 53' is opened, the frangible seals 60 and 62 will break apart before the wrapper 30 will tear or rip.

Unique applications may require the use of frangible seals. For example, in FIG. 10, when the first and second seals, 60 and 62 respectively, are permanent seals, the package 53' can only be opened by tearing the material between the slits forming the first and second lines of perforations, 76 and 78 respectively. If the first and second seals, 60 and 62 respectively, are made to be frangible, the frangible seals 60 and 62 would break apart before the wrapper 30 breaks at the first and second lines of perforations, 76 and 78 respectively. If this condition is present, then it provides another alternative means for the user to open the package. However, for purposes of this invention, the preferred method of opening the package 53' is that the first and second lines of perforations, 76 and 78 respectively, will break apart before the first and second seals, 60 and 62 respectively, break apart.

It should also be noted that when the first and second seals, 60 and 62 respectively, are permanent type seals, the first and second lines of perforation, 76 and 78 respectively, should be spaced at least about 0.1 inches (about 2.5 mm) away from each of the first and second seals, 60 and 62 respectively. The reason for this is that it will allow the width of the strips 80 and 82 to be of a sufficient dimension so that the user can grasp and tear off the strips 80 and 82 from the main portion of the wrapper 30. However, it should be noted that the distance that the first and second lines of perforation, 76 and 78 respectively, are aligned away from the first and second seals, 60 and 62 respectively, should not be so great that when the user tears off the strips, 80 and 82 respectively, that there will not be sufficient material left to wrap up the soiled product.

Figure 11:
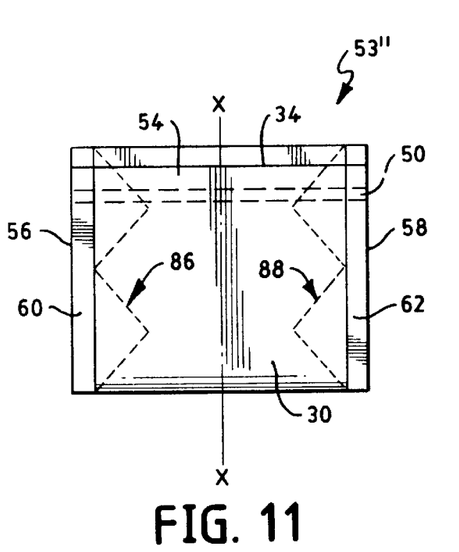
FIG. 11 is still another embodiment of the package shown in FIG. 6 wherein the first and second lines of perforation have a non-linear orientation such as a saw tooth or stepped arrangement.

Referring to FIG. 11, still another embodiment of a package 53" is shown which is similar to the embodiment shown in FIG. 10, except that it contains first and second lines of perforations, 86 and 88 respectively, which are formed in a nonlinear fashion. In other words, each of the first and second lines of perforations, 86 and 88 respectively, are arranged in a saw-tooth or zigzag pattern relative to the first and second side edges, 56 and 58 respectively, of the package 53". It should be noted that both the first and second lines of perforations, 86 and 88 respectively, are shown to be mirror images of one another, although this is not necessary. Each of the first and second lines of perforations, 86 and 88 respectively, can be of a different configuration if desired. The saw-tooth arrangement of each of the first and second lines of perforations, 86 and 88 respectively, resembles the teeth of a saw or the serrated edge of a knife. Another way of forming the nonlinear first and second lines of perforations, 86 and 88 respectively, is to use angled sections of a line such that a staircase arrangement is obtained. By making the first and second lines of perforations, 86 and 88 respectively, nonlinear, one can form an undulating or irregular edge along the wrapper 30 which may be visually and aesthetically pleasing to the ultimate user.

Figure 12:
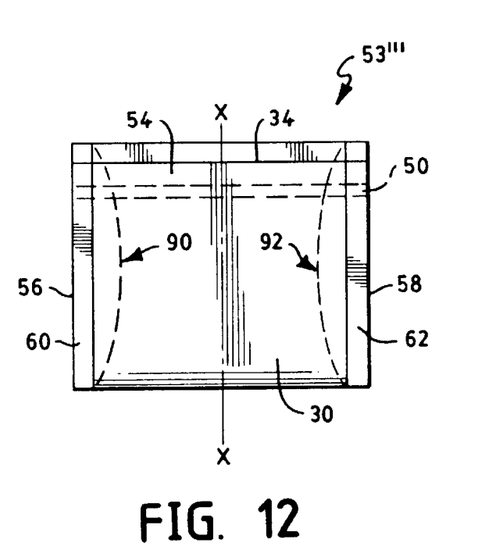
FIG. 12 is still another alternative embodiment of the package shown in FIG. 6 wherein each of the first and second lines of perforations are nonlinear and are positioned adjacent to the first and second seals.

Referring now to FIG. 12, still another embodiment of a package 53''' is shown wherein the package 53''' contains first and second lines of perforations, 90 and 92 respectively, which are also nonlinear and which are formed so as to have an arcuate or curvilinear shape. As shown in FIG. 12, the first and second lines of perforations, 90 and 92 respectively, have a convex and a concave configuration. The first and second lines of perforations, 90 and 92 respectively, can be formed as a smooth arc, having a semicircular or ellipsoidal portion or some other curvilinear configuration. The first and second lines of perforations, 90 and 92 respectively, should be relatively smooth, arcuate segments which can be a mirror image of one another. It should also be noted that the first and second lines of perforations, 86 and 88 respectively, as well as the first and second lines of perforations, 90 and 92 respectively, should be formed adjacent to the seals, 60 and 62 respectively. The first and second seals, 60 and 62 can be of either the permanent or frangible design.

Figure 13:
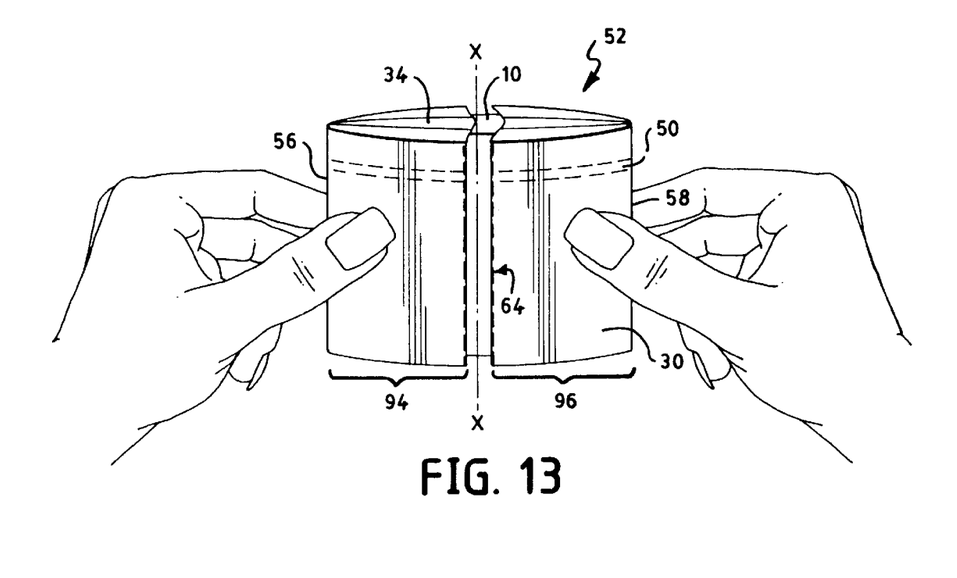
FIG. 13 is a schematic view representing one way of opening the package shown in FIG. 7 which includes grasping the side edges of the package and then pulling the wrapper apart so that it breaks at the single line of perforation.

Referring now to FIG. 13, a schematic representation is shown with the user grasping the two opposite side portions of the package 52 adjacent to the first and second side edges, 56 and 58 respectively. The user, by a quick outward movement of her two hands, can snaps the wrapper 30 such that it causes it to break along the first line of perforations 64. This action tears the wrapper 30 into two individual segments, 94, and 96 respectively, thereby exposing the absorbent article 10.

Figure 14:
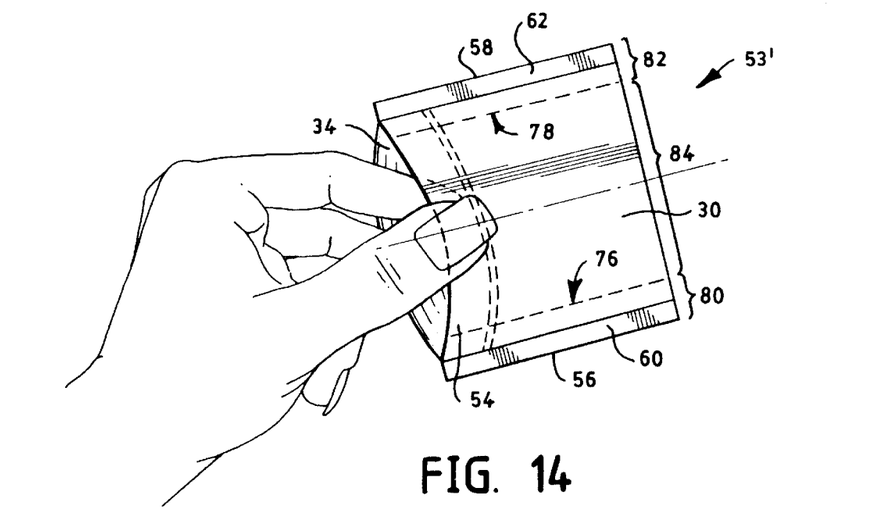
FIG. 14 is a schematic view representing a way of opening the package shown in FIG. 10 which includes inserting one or more fingers under the flap and grasping the flap between her thumb and finger(s) and pulling outward to break the two lines of perforations.

Referring to FIG. 14, the package 53' is illustrated having the user's index and middle finger inserted into the flap 54 and extending beyond the attachment device 50. In this case, the releasable attachment device 50 can be a line of adhesive which is easily broken apart. The user then grasps the wrapper 30 between her two fingers and her thumb so that while holding the remainder of the package 53' in her other hand, she can pull upwards and outwards such that the flap 54 moves away from the first and second seals, 60 and 62 respectively, causing the wrapper 30 to break along the first and second lines of perforations, 76 and 78 respectively. As the fingers and thumb pull the material apart from the package 53', the lines of perforations, 76 and 78 respectively, will continue to break the material located between the adjacent slits such that the wrapper 30 will be separated into three individual segments 80, 82 and 84. Two of those segments will be the small end strips 80 and 82 while the third segment will be the larger central portion 84.

It should be noted that for absorbent articles 10, such as sanitary napkins, it is preferable that the package 53' be of a relatively small size, preferably less than about the size of a 4×4 inch (100 mm×100 mm) rectangle. In this size package, the first and second lines of perforations, 76 and 78 respectively, will be spaced apart less than about 4 inches (about 100 mm) from each other. More preferably, the first and second lines of perforations, 76 and 78 respectively, will be spaced apart less than about 3.5 inches (about 89 mm) from each other, and most preferably, they will be spaced apart less than about 3 inches (about 76 mm) from each other.

Figure 15:
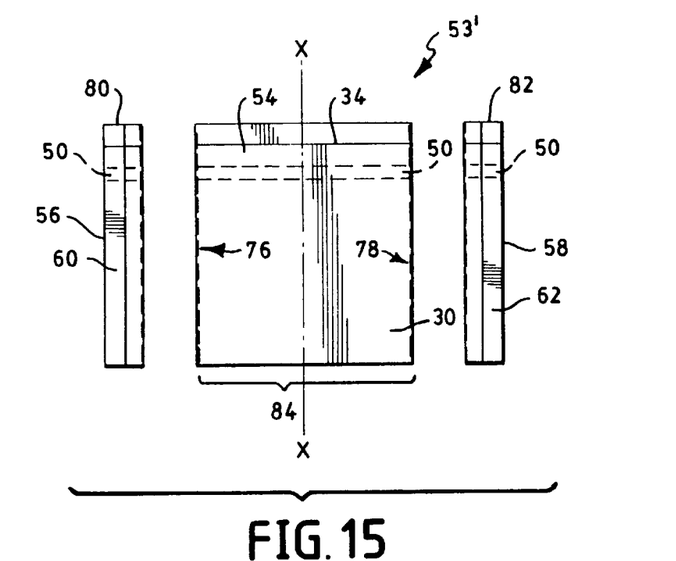
FIG. 15 is a depiction of the package shown in FIG. 10 after the first and second lines of perforations have been completely broken.
Figure 16:
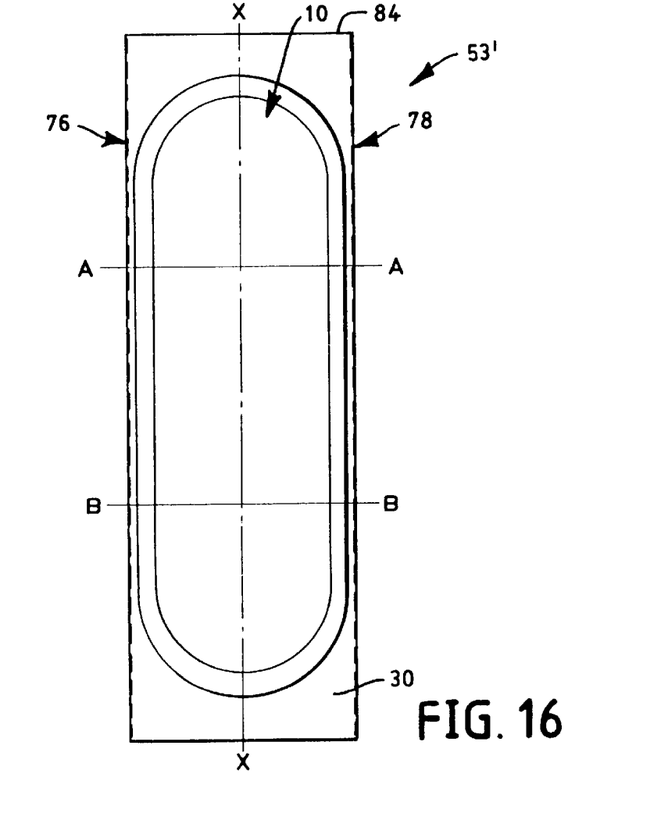
FIG. 16 is a top view depicting the absorbent article and the wrapper being unfolded after the two side strips have been broken away at the first and second lines of perforations.

Referring now to FIGS. 15 and 16, an alternative way to open the package 53' is illustrated. In this alternative method, the user grasps the strip 80 between her index finger and thumb and tears it along the first line of perforations 76. The user then grasps a portion of the strip 82 between her index finger and thumb and simultaneously or sequentially tears it along the second line of perforations 78 thereby separating the strip 82 from the larger central portion 84. The two individuals strips 80 and 82 can then be discarded. The larger strip 84 is separated from the absorbent article 10 by pulling on the flap 54 to break the attachment device 50. The wrapper 30 and the absorbent article 10 can then be unfolded, as is shown in FIG. 16, such that the absorbent article 10 is completely opened relative to the wrapper 30. The user would then remove the absorbent article 10 from the wrapper 30, remove the release strip 28, and attach the absorbent article 10 onto the inner crotch portion of her undergarment.

The use of one or more lines of perforations 64, 66 and 68 or 76 and 78 allows the package 52, 52', 53', 53" or 53''' to be opened in an efficient, quiet, and easy manner. The lines of perforations 64, 66 and 68 or 76 and 78 can be formed by the use of a perforation wheel or blade having a notched outer periphery or surface. The land portions of the blade or knife used to form the perforations can be in the range of about 0.0001 inches to about 0.001 inches (about 0.002 mm to about 0.02 mm), preferably, between about 0.0003 inches to about 0.008 inches (about 0.007 mm to about 0.2 mm), and more preferably, the length of each blade can be from between about 0.0003 inches to about 0.0005 inches (about 0.007 mm to about 0.01 mm). As mentioned earlier, the length of each slit does not have to be of the same length or width as the adjacent slit but can vary.

The pattern of the slits can also vary such that several of the slits can be identical in shape and appearance. A large land area can be presence between some of the slits if desired. This could yield an intermittent slit pattern. Either the intermittent or continuous slit arrangement can be utilized depending upon the strength needed to separate the perforations. One would want to form the lines of perforations such that the material located between the perforations will not break under a very small amount of pressure but will yield before a very large amount of pressure is required. The amount of pressure needed to break the material located between adjacent slits will be determined upon the type of product which is packaged, the material from which the wrapper is formed, the age and makeup of the consumer who will have to open the package, as well as other factors. Some of these other factors include: the presence of a coating which may be present on the wrapper, the shape and configuration of the lines of perforations, and the width of the strip(s) 80 or 82 which the consumer is required to grasp in order to tear open the package. For example, if the width of the strips 80 and 82 is very small, it may require a greater force to break the line of perforations, 76 and 78 respectively, than if more material was present. When the strips 80 and 82 are wider, the consumer may be able to more easily grasp the material forming the strips 80 and 82 and thereby less force may be needed to separate the strips 80 and 82 from the remainder of the wrapper 30.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

We claim:

1. An individually wrapped absorbent article comprising:
   a) an absorbent article having first and second ends, first and second sides and first and second major surfaces, said second major surface of said article having a garment adhesive secured thereto;
   b) a release strip removably secured to said garment adhesive to prevent premature contamination of said adhesive before said absorbent article is secured to an undergarment;
   c) a wrapper having first and second ends, first and second sides and first and second major surfaces, said first surface of said wrapper being positioned adjacent to said release strip with said first and second ends of said wrapper extending beyond said first and second ends, respectively, of said absorbent article and said first and second sides of said wrapper extending beyond said first and second sides, respectively, of said absorbent article;
   d) an attachment device secured to said second major surface of said wrapper approximate said first end thereof, said wrapper and said article being folded together about two fold axes such that said first major surface of said wrapper contacts said attachment device and is releasably secured thereto to form a package, said package having first and second side edges aligned approximately parallel to said first and second sides of said article, respectively;
   e) first and second permanent seals securing said first and second side edges of said package together, respectively; and
   f) first and second spaced apart lines of perforations formed in said wrapper which provide an easy open feature for said package, said first line of perforations being aligned adjacent to said first permanent seal and said second line of perforations being aligned adjacent to said second permanent seal.

2. The individually wrapped absorbent article of claim 1 wherein each of said lines of perforations is comprised of a series of slits each having a length of less than about 0.001 inches.

3. The individually wrapped absorbent article of claim 1 wherein said first and second lines of perforations are linear.

4. The individually wrapped absorbent article of claim 1 wherein said first and second lines of perforations are non-linear.

5. The individually wrapped absorbent article of claim 1 wherein each of said first and second lines of perforations are spaced at least about 0.1 inches away from each of said first and second permanent seals, respectively.

* * * * *